United States Patent [19]

Walba et al.

[11] Patent Number: 4,705,874

[45] Date of Patent: Nov. 10, 1987

[54] SYNTHESIS OF NEW LIQUID CRYSTAL MATERIALS POSSESSING PHENYLBENZOATE OR BIPHENYL CORE UNITS AND (2,3)-EPOXYALKYLOXIRANEMETHANOL CHIRAL TAILS

[75] Inventors: David M. Walba; Rohini Vohra, both of Boulder, Colo.

[73] Assignee: University Patents, Inc., Westport, Conn.

[21] Appl. No.: 925,937

[22] Filed: Oct. 31, 1986

Related U.S. Application Data

[62] Division of Ser. No. 782,348, Oct. 1, 1985, Pat. No. 4,638,073.

[51] Int. Cl.$^4$ .................. C07D 303/12; C07D 303/32; C09K 19/34; C09K 19/12
[52] U.S. Cl. .............................. 549/557; 252/299.01; 252/299.61; 252/299.66; 549/555; 549/556
[58] Field of Search ...................... 252/299.61, 299.66, 252/299.01; 549/557; 350/350 S

[56] References Cited

U.S. PATENT DOCUMENTS

| | | | |
|---|---|---|---|
| 4,471,130 | 9/1984 | Katsuki et al. | 549/523 |
| 4,556,727 | 12/1985 | Walba | 252/299.67 |
| 4,565,425 | 1/1986 | Petrzilka et al. | 350/350 R |
| 4,576,732 | 3/1986 | Tsogai et al. | 252/299.66 |
| 4,613,209 | 9/1986 | Goodby et al. | 350/350 S |
| 4,621,901 | 11/1986 | Petrzilka et al. | 350/350 R |
| 4,654,421 | 3/1987 | Taraka et al. | 544/335 |

OTHER PUBLICATIONS

Goodby et al, Liq. Cryst. Ord. Fluids, vol. 4, pp. 1–32, (1984).

Primary Examiner—Teddy S. Gron
Assistant Examiner—J. E. Thomas
Attorney, Agent, or Firm—George M. Yahwak

[57] ABSTRACT

Ferroelectric (chiral) smectic liquid crystal compounds having an achiral core and chiral tail units derived from (2,3)-epoxyalkyloxiranemethanols possess a high ferroelectric polarization density. These newly made compounds exhibit high speed, multistate electro-optic switching properties which make them ideally suited to certain electro-optic display device applications.

24 Claims, No Drawings

SYNTHESIS OF NEW LIQUID CRYSTAL MATERIALS POSSESSING PHENYLBENZOATE OR BIPHENYL CORE UNITS AND (2,3)-EPOXYALKYLOXIRANEMETHANOL CHIRAL TAILS

This is a division of application Ser. No. 782,348 filed Oct. 1, 1985 now U.S. Pat. No. 4,638,073.

Liquid crystals have found use in a variety of electro-optical and display device applications, in particular those which require compact, energy efficient, voltage-controlled light valves such as watch and calculator displays. These devices are based upon the dielectric alignment effects in nematic, cholesteric, and smectic phases of the crystal compound in which, by virtue of the dielectric anisotropy, the average molecular long axis of the compound takes up a preferred orientation in an applied electric field. Since the coupling of an applied electric field by this mechanism is rather weak, thereby providing the energy efficiency for these devices, the resultant electro-optical response time for these devises is too slow for many other potential applications.

Liquid crystal displays have a number of unique characteristics, including low voltage and low power of operation, which makes them perhaps the most promising of the non-emissive electro-optical display candidates available with today's technology. However, the slow response and insufficient nonlinearity in liquid crystal displays have been serious limitations to many potential applications. The lack of speed becomes especially important in proportion to the number of elements that have to be addressed in a device; this results in increasingly impractical production costs for the potential use of such devices in flat-panel displays for use in video display terminals, oscilloscopes, radar, and television screens.

It has recently been shown (see N. A. Clark and S. T. Lagerwall, Appl. Phys. Lett. 36:899 (1980), and U.S. Pat. No. 4,367,924) that electrooptic effects with submicrosecond switching speeds are achievable using the technology of ferroelectric liquid crystals. Some ferroelectric liquid crystal display structures, in addition to the high speed (about one thousand times faster than currently used twisted nematic devices) reported by these investigators, exhibit bistable, threshold sensitive switching, making them potential candidates for matrix addressed light valves containing a large number of elements for passive display of graphic and pictorial information, as well as for optical processing applications.

A basic requirement for application of ferroelectric liquid crystals in such devices is the availability of chemically stable liquid crystal compounds which exhibit ferroelectric phases over a substantial temperature range about room temperature. Ideally, these compounds, which must be chirally asymmetric to be ferroelectric, would exhibit a large ferroelectric dipole density ($P_o$) in order to optimize coupling to an applied electric field, and a low orientational viscosity ($V_o$) in order to optimize response times.

While some useful liquid crystal materials have been reported, materials having optimum response times are still being sought. This is partly due to the relatively low dipole densities of many of the known materials.

It is the object of the present invention to describe a class of chirally asymmetric liquid crystal having a high dipole density and low orientational viscosity.

It is a further object of the present invention is to disclose a class of compounds by which enantiomerically enriched units may be incorporated into the molecular framework of chirally asymmetric liquid crystals.

These and other objects and advantages of the present invention will become more apparent, and more readily appreciated from the following detailed description of the presently preferred exemplary embodiments of the present invention.

The chirally asymmetric liquid crystal compounds of the present invention are formed by the incorporation of enantiomerically enriched tail units derived from the readily available and inexpensive non-racemic (2,3)-3-alkyloxiranemethanols (see T. Katsuki and K. B. Sharpless, *J. Am. Chem. Soc.* 102:5976 (1980) and U.S. Pat. No. 4,471,130) into a liquid crystal molecular framework. More specifically, we have found that (1) attachment of an enantiomerically enriched cis- or trans-(2,3)-3-alkyloxiranemethanol unit to the para position of a phenyl group of a phenyl benzoate core unit or (2) attachment by an ester linkage to a 4-alkyloxy-4-biphenylcarboxylate core unit, will confer the desired property of a high dipole density to the chirally asymmetric liquid crystal compounds.

The intermediate compound by which the enantiomerically enriched epoxide units are incorporated into the phenyl benzoate liquid crystal molecular framework are also part of the present invention. More specifically, these compounds are of the general Formula I:

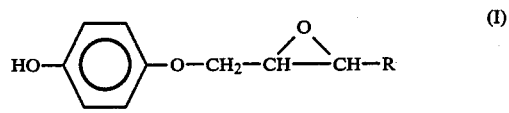
(I)

wherein R may be any alkyl of one to twelve carbon atoms, and the epoxide ring may be cis- or trans-disubstituted. For example, R may be methyl, ethyl, propyl, butyl, pentyl, hexyl, heptyl, octyl, nonyl, decyl, undecyl, or dodecyl radicals. Furthermore, in those instances when the alkyl radical may possess structural isomerism, such as in those alkyls having three or more carbon atoms, such isomers as, for example, isopropyl, are also included within the R definition of alkyl.

Although the intermediate compounds according to the present invention may be selected to contain an R radical from a relatively large class of alkyl substituents, for the purposes of the ferroelectric smectic liquid crystal compounds of the present invention R is preferred to be an alkyl radical containing from one to seven carbon atoms.

The incorporation of enantiomerically enriched tail units derived from (2,3)-3-alkyloxiranemethanols into the liquid crystal molecular framework results in ferroelectric smectic liquid crystals of the general Formulas II and III:

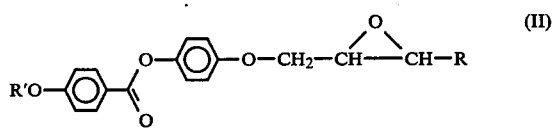
(II)

-continued

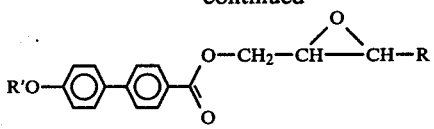

wherein R is an alkyl group of one to seven carbon atoms, and R is an alkyl of five to twelve carbon atoms.

The compounds according to the present invention are prepared following the exemplary synthesis flow pathways shown below.

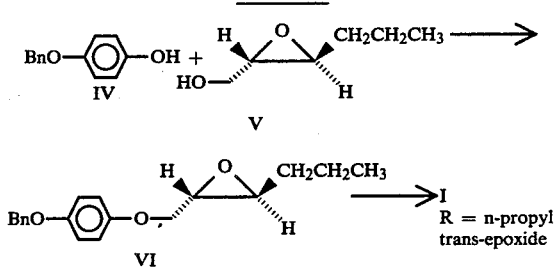

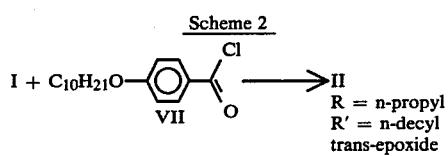

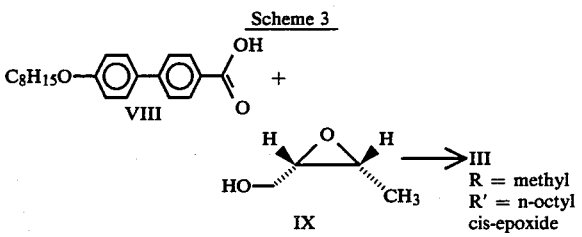

In these synthesis pathways, the following abbreviation is used: Bn=benzyl.

In general terms, compounds of Formula I are prepared by coupling of p-benzyloxyphenol with epoxy alcohols (for example, the compound of Formula V) according to the general procedure of Mitsonobu (see O. Mitsonobu, Synthesis, 1 (1981) affording compounds of type VI, followed by debenzylation by catalytic hydrogenation to give I.

Coupling of phenols I with p-alkoxybenzoyl chlorides of type VII then affords the liquid crystal compounds II.

The liquid crystal compounds III are prepared by direct coupling of epoxyalcohols (for example, the compounds of Formula IX) with p-biphenylcarboxylic acids VIII by the Mitsonobu procedure.

The following examples and procedures are presented in order to provide a more complete understanding and illustration of the present invention.

EXAMPLE I

This example illustrates the procedure for coupling of the compounds of Formulas IV and V.

To a three-neck flask flushed with argon and fitted with a magnetic stir bar was added 30 ml of dry THF, 1.379 gm (6.9 mmol) of p-benzyloxyphenol (the compound of Formula IV), 0.8 gm (6.0 mmol) of (2S,3S)-3-prophloxiranethanol (the compound of Formula V), and 1.98 gm (7.59 mmol) of triphenylphosophine. The resulting solution was heated to reflux and 1.2 ml (2.32 gm, 7.59 mmol) of diethyl azodicarboxylate was added over a period of 7 hr. After the addition was complete the reaction mixture was allowed to cool to room temperature and stir for an additional two days under argon. The solvent was then removed, and the residue purified by flash chromatography on silica gel using 85.15 hexanes/ethyl acetate as eluent. In this manner 1.6 gm (78%) of 4-benzyloxy-1-[2S,3S)-epoxy]-hexyloxybenzene (the compound of Formula VI) was obtained.

EXAMPLE II

This example illustrates the procedure for debenzylation of compounds of Formula VI.

To a glass hydrogenator fitted with a magnetic stir bar was added 0.67 gm (2.2 mmole) of p-benzyloxy-[(2S,3S)-epoxy]-hexyloxy-benzene (the compound of Formula VI), 5 ml of ethanol and 100 mg of 10% Pd on carbon. The reaction vessel was evacuated and hydrogen gas was introduced. The mixture was allowed to stir for 3-4 hr under a positive pressure of hydrogen gas (the reaction was judged complete by TLC-the product had Rf=)0.28 eluting with 7:3 hexanes/ethyl acetate, to give 0.35 gm (75%) of p-[(2S,3S)-epoxy]-hexyloxphenol (the compound of Formula I).

EXAMPLE III

This example illustrates the procedure for the coupling of compounds of Formulas I and VII.

To a 10 ml flask fitted with a magnetic stir bar and charged with 97 mg (0.5 mmol) of p-[2S,3S)-epoxy]-hexyloxyphenol (the compound of Formula I), was added 2 ml of dry dichloromethane, 0.5 ml of triethylamine and a few crystals of DMAP. To the resulting solution was added 148 mg (0.5 mmol) of p-decyloxybenzoyl]chloride (the compound of Formula VII) in 1 ml of dry dichloromethane. The mixture was allowed to stir for 1 hr, after which the solvent was removed. The residue was treated with 5% aqueous hydrochloric acid and the product was extracted into 2×25 ml portion of ether. The combined ether layers were washed with 5% aqueous CHI, then twice with 5% aqueous sodium hydroxide, then with water, and dried over anhydrous sodium sulfate. Filtration and removal of solvent, gave 0.22 gm (95%) of crude product. This material was purified by flash chromatography using 9:1 hexanes-/ethyl acetate as eluent. The product was further purified by crystallization from ethanol. After four recrystallizations, p-[(2S,3S)-epoxy]-hexyloxyphenyl-p-decyloxybenzoate (the compound of Formula II) with an isotropic liquid to smectic A transition temperature range of less than 2° C. was obtained.

EXAMPLE IV

This example illustrates the procedure for coupling of the compounds of Formulas VIII and IX.

A small argon flushed flask equipped with a magnetic stir bar was charged with 79 mg (0.3 mmol) of triphenylphosphine, 52 mg (0.3 mmol) of diethyl azodicarboxylate, and 5 ml of THF. The resulting solution was allowed to stir for 5 min before a solution prepared from 48 mg (0.147 mmol) of octyloxybiphenylcarboxylic acid (the compound of Formula VIII) and 13 mg (0.147 mmol) of 2S,#R)-3-butyloxira nemethanol (the compound of Formula IX) in 2 ml of dry THF was added dropwise. The reaction mixture was then cooled and the solvent removed. The resulting crude product was purified by chromatography on silica gel using 85:15 hexanes/ethyl acetate as eluent, affording 48 mg (83%) of 4'-octyloxy-4-[(2S,3R)-epoxy]-butyl-biphenylcarboxylate (the Compound of Formula III). Analytically pure material was obtained by crystallization from 4:1 ethanol/hexanes.

The following Table I gives the phase transition temperatures for several of the compounds according to general Formulas II and III in order to illustrate the liquid crystal properties of the new compounds. In addition, it has been shown that compound II (R''=n-octyl, R'''=n-propyl) has a positive dipole density of 30 ncoul/cm$^2$, among the highest of any compounds reported to date.

In Table I, phase transition temperatures are given in °C. (I=isotropic liquid, A-smectic A phase, N*-chiral nematic phase, C*-chiral smectic C phase, and X-crystalline solid).

TABLE I

| Compounds II, cis epoxide | | | | | | |
|---|---|---|---|---|---|---|
| R = methyl, R' = decyl | I | 68 | A | 35 | X | |
| R = ethyl, R' = decyl | I | 49 | A | 44 | X | |
| R = propyl, R' = decyl | I | 43 | A | 37 | X | |
| Compounds II, trans epoxide | | | | | | |
| R = propyl, R' = decyl | I | 120 | N* | 81 | C* 62 | X |
| Compounds III, cis epoxide | | | | | | |
| R = methyl, R' = decyl | I | 91.4 | A | 60 | X | |
| R = methyl, R' = octyl | I | 97 | A | 56 | X | |
| R = ethyl, R' = octyl | I | 96.5 | A | 90 | X | |
| R = propyl, R' = octyl | I | 98 | A | 94 | X | |

As shown in the table, two of the new materials have stable ferroelectric phases. While these materials have ferroelectric phases at temperatures well above room temperature, the high dipole density exhibited by one of them makes this class of compounds important as components in high-performance room temperature ferroelectric liquid crystal eutectic mixtures. It is important to note that either enantiomer of any of the described chiral compounds can be readily obtained, allowing the sign of the polarization density to be easily adjusted to optimize the ferrolectric dipole density of mixtures incorporating these compounds.

Thus, while the present asymmetrical liquid crystal compounds have been defined in their pure state. the present invention is meant to encompass liquid crystal formulations in which the compounds of the present invention are used in mixture with one another, or formulations in which a compound of the present invention is used in mixture with other, previously known or unknown liquid crystal compounds.

Furthermore, while only a single enantiomer of each chirally asymmetrical compound has been prepared, the present invention is meant to encompass both enantiomers of each compound.

From the foregoing description, one skilled in the art can easily ascertain the essential characteristics of our invention and without departing from the spirit and scope thereof, can make various changes and/or modifications to the invention for adapting it to various usages and conditions. Accordingly, such changes and modifications are properly intended to be within the full range of equivalents of the following claims.

Having thus described our invention and the manner and process of making and using it in such full, clear, concise, and exact terms as to enable any person skilled in the art to which it pertains, or with which it is most closely connected, to make and use the same, and having set forth the best modes for carrying out our invention:

We claim:
1. A compound of the formula:

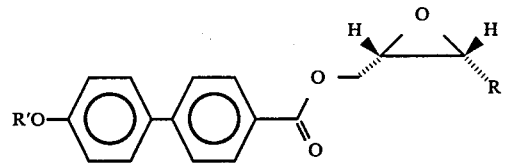

wherein R is an alkyl of one to seven carbon atoms, and R' is an alkyl of five to twelve carbon atoms.

2. A compound according to claim 1 wherein R contains one to three carbon atoms, and R' contains eight to twelve carbon atoms.

3. A compound according to claim 2 wherein R is —CH$_3$.

4. The compound according to claim 3 wherein R' contains eight carbon atoms.

5. The compound according to claim 3 wherein R' contains ten carbon atoms.

6. A compound according to claim 2 wherein R is —CH$_2$CH$_3$.

7. The compound according to claim 2 wherein R' contains ten carbon atoms.

8. The compound according to claim 2 wherein R' contains twelve carbon atoms.

9. A compound according to claim 2 wherein R is —CH$_2$CH$_2$CH$_3$.

10. The compound according to claim 9 wherein R' contains eight carbon atoms.

11. The compound according to claim 9 wherein R' contains ten carbon atoms.

12. The compound according to claim 9 wherein R' contains twelve carbon atoms.

13. A compound of the formula:

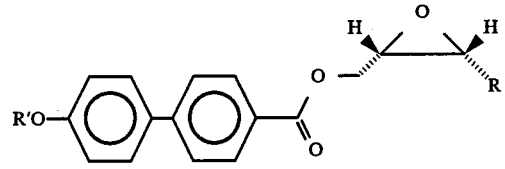

wherein R is an alkyl of one to seven carbon atoms and R' is an alkyl of five to twelve carbon atoms.

14. A compound according to claim 13 wherein R contains one to three carbon atoms, and R' contains eight to twelve carbon atoms.

15. A compound according to claim 14 wherein R is —CH$_3$.

16. The compound according to claim 15 wherein R' contains eight carbon atoms.

17. The compound according to claim 15 wherein R' contains ten carbon atoms.

18. A compound according to claim 14 wherein R is —CH$_2$CH$_3$.

19. The compound according to claim 18 wherein R' contains ten carbon atoms.

20. The compound according to claim 18 wherein R' contains twelve carbon atoms.

21. A compound according to claim 14 wherein R is —CH$_2$CH$_2$CH$_3$.

22. The compound according to claim 21 wherein R' contains eight carbon atoms.

23. The compound according to claim 21 wherein R' contains ten carbon atoms.

24. The compound according to claim 21 wherein R' contains twelve carbon atoms.

* * * * *